(12) United States Patent
Weller et al.

(10) Patent No.: US 7,264,925 B2
(45) Date of Patent: Sep. 4, 2007

(54) METHOD FOR ANALYSIS OF OLIGONUCLEOTIDE ANALOGS

(75) Inventors: Dwight D. Weller, Corvallis, OR (US); Todime Muralimohan Reddy, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 0 days.

(21) Appl. No.: 09/943,458

(22) Filed: Aug. 30, 2001

(65) Prior Publication Data

US 2002/0110819 A1  Aug. 15, 2002

Related U.S. Application Data

(60) Provisional application No. 60/229,245, filed on Aug. 30, 2000.

(51) Int. Cl.
*C12Q 1/68* (2006.01)
(52) U.S. Cl. ......................................................... 435/6
(58) Field of Classification Search ............... 435/6, 435/91.1, 70.1, 320.1, 91.2; 528/391, 403, 528/405, 406; 530/350; 536/23.4; 356/344; 436/161

See application file for complete search history.

(56) References Cited

U.S. PATENT DOCUMENTS

| | | | | |
|---|---|---|---|---|
| 4,279,724 A | * | 7/1981 | Hearn ........................ 204/180 |
| 5,034,506 A | * | 7/1991 | Summerton .................. 528/391 |
| 5,405,938 A | * | 4/1995 | Summerton .................. 528/406 |
| 5,686,242 A | * | 11/1997 | Bruice et al. ................... 435/6 |
| 5,874,213 A | * | 2/1999 | Cummins et al. .............. 435/6 |
| 5,932,413 A | * | 8/1999 | Celebuski ....................... 435/6 |
| 5,986,053 A | * | 11/1999 | Ecker et al. ................. 530/350 |
| 6,263,286 B1 | * | 7/2001 | Gilmanshin .................. 702/19 |
| 6,342,370 B1 | * | 1/2002 | Connolly .................... 435/69.1 |
| 6,365,351 B1 | * | 4/2002 | Iversen .......................... 435/6 |
| 6,613,508 B1 | * | 9/2003 | Ness et al. ...................... 435/6 |

FOREIGN PATENT DOCUMENTS

| | | | |
|---|---|---|---|
| WO | WO9636734 A1 | * | 11/1996 |
| WO | WO97/12995 | | 4/1997 |
| WO | WO9712995 A1 | * | 4/1997 |
| WO | WO98/04571 | | 2/1998 |
| WO | WO98/38334 | | 9/1998 |

OTHER PUBLICATIONS

Carlsson, C., et al., *Nature 380*, (1996).
Orum, H., et al., *BioTechniques* 19(3):472-480 (1995).
Bio-Rad Laboratories, *Bio-Rad Technical Bulletin* (*Online*) pp. 1-4 (1998).
WO 02/18656, International Search Report dated Mar. 2002.

* cited by examiner

*Primary Examiner*—Young J. Kim
(74) *Attorney, Agent, or Firm*—Perkins Coie LLP

(57) ABSTRACT

Disclosed are methods for separating, detecting, quantitating and/or isolating predominantly uncharged oligonucleotide analogs, by resolving duplexes of such molecules with complementary or near-complementary DNA or charged DNA analogs. The DNA or charged analog may be labeled for detection purposes.

19 Claims, 12 Drawing Sheets

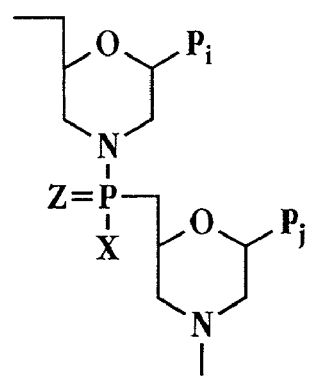
Fig. 2A-A
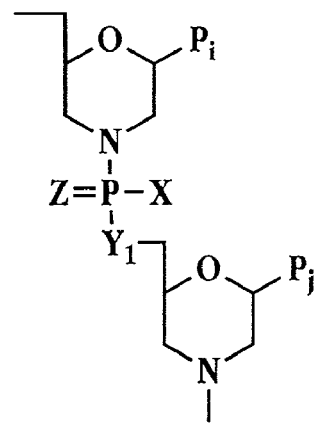
Fig. 2B-B
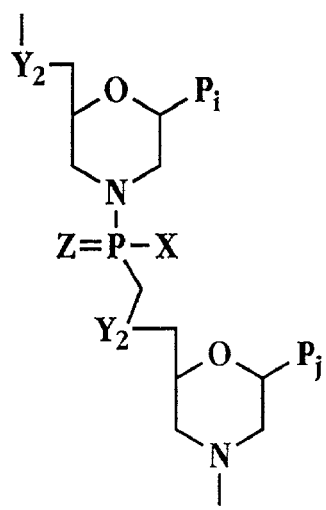
Fig. 2C-C
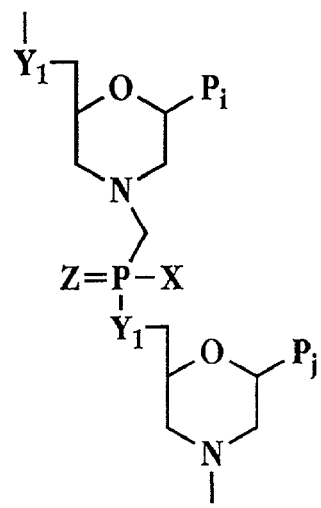
Fig. 2D-D/E-E

```
TGCAACTCCCCGTAGCAGCG       charged
 ||||||||||||||||||
ACGTTGAGGGGCATCGTCGC       uncharged TGCAACTCCCCGTAGCAGCG       charged
 |||||||||||||||||
ACGTTGAGGGGCATCGTC         uncharged TGACAACTCCCCGTAGCAGCG      charged
  ||||||||||||||||
 ACGTTGAGGGGCATCG          uncharged TGCAACTCCCCGTAGCAGCG       charged
 ||||||||||||||||
ACGTTGAGGGGCAT             uncharged TGCAACTCCCCGTAGCAGCG       charged
     |||||||||||||
    GTTGAGGGGCAT            uncharged TGCAACTCCCCGTAGCAGCG       charged
          ||||||||
         TGAGGGGCATCGTCGC  uncharged
```

Fig. 3

```
CCCGTAGCAGCCGNNNN      charged
|||||||||||||
ACGTTGAGGGGCATCGTCGC   uncharged CCCGTAGCAGCCGNNNN      charged
|||||||||||||
ACGTTGAGGGGCATCGTC     uncharged CCCGTAGCAGCCGNNNN      charged
|||||||||||||
ACGTTGAGGGGCATCG       uncharged

[NNNN is optional]
```

Fig. 4A

```
  CCGTAGCAGC            charged
  |||||||||
ACGTTGAGGGGCATCGTCGC    uncharged C-
       ^
  CCGTAGAGC             charged
  |||||||||
ACGTTGAGGGGCATCTCGC     uncharged
```

Fig. 4B

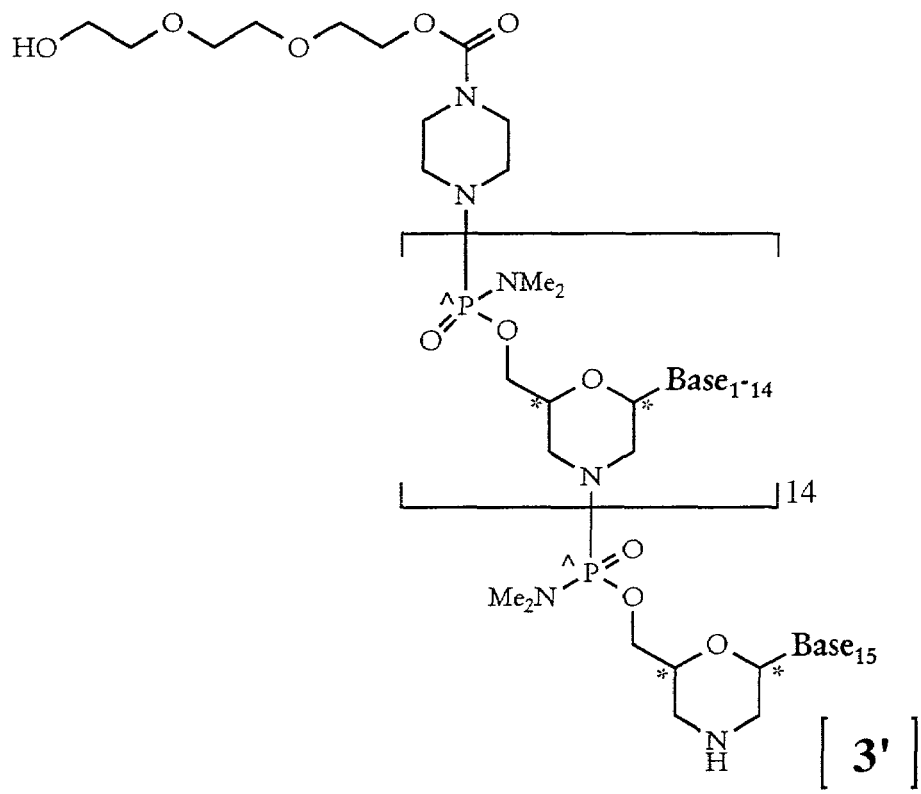
Base$_{1-15}$ = GAGGGGCATCGTCGC (5' → 3')
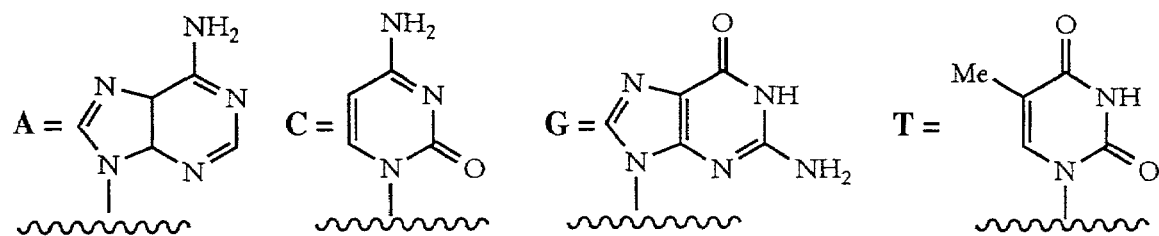
Fig. 11

METHOD FOR ANALYSIS OF OLIGONUCLEOTIDE ANALOGS

This application claims priority to U.S. provisional application Ser. No. 60/229,245, filed Aug. 30, 2000, which is hereby incorporated by reference in its entirety.

FIELD OF THE INVENTION

The present invention relates to methods for separating, quantitating and/or isolating oligonucleotide analogs having a substantial amount, preferably 50% or more, of uncharged subunits. In particular, the invention relates to chromatographic or electrophoretic methods of separation.

BACKGROUND OF THE INVENTION

Numerous charged-based separation methods are available for use with biopolymers which bear a charge at neutral or near-neutral pH, such as nucleic acids and the majority of proteins. These include, for example, various modes of electrophoresis, isoelectric focusing, and ion exchange. Such methods, however, cannot generally be employed for substantially uncharged oligonucleotide analogs without prior ionization of the molecules. For example, current methods of ion exchange separation of uncharged oligonucleotides require ionization of the molecules at either high pH (>11), at which G and T bases ionize, or at low pH (<3), at which C and A bases ionize. Some uncharged oligonucleotide analogs, such as, for example, phosphoramidate- or phosphorodiamidate-linked oligomers, are not stable at these low pH's. Accordingly, there is a need for methods of separation of such uncharged molecules that can be can be carried out under mild conditions, at neutral or near neutral pH.

SUMMARY OF THE INVENTION

The present invention includes, in one aspect, a method of analyzing and/or separating a population of oligomeric analyte molecules, wherein the molecules are composed of linked subunits of which at least 50% are uncharged at neutral or near-neutral pH, and are able to hybridize via Watson-Crick base pairing with a specific probe molecule which is a nucleic acid or a charged nucleic acid analog. The method comprises the steps of (a) applying to a charge-bearing separation medium a mixture of (i) the population of analyte molecules and (ii) the probe, under conditions such that complementary or near-complementary regions of the probe and at least one analyte molecule are stably hybridized, thereby forming a mixture of species selected from probe-analyte duplex, single-stranded analyte, single-stranded probe, and combinations thereof, and (b) separating the species within the medium.

Preferably, the probe has a length and sequence such that its duplexes with different analyte molecules differ with respect to the presence, length or position of an unhybridized portion of the nucleic acid. For detection purposes, the probe is labeled, preferably with a fluorescent label, e.g. fluorescein. The label is typically at a terminus of the probe, e.g. the 5' terminus.

In a typical separation, each analyte molecule has a nucleotide sequence which is selected from the group consisting of: a selected sequence, different length fragments of the selected sequence, internal deletion or insertion variants of the selected sequence, mutation variants of the selected sequence, and combinations thereof. Such deletion, insertion or mutation variants generally contain at most one such deletion or mutation per 8 nucleotides of the selected sequence. In one embodiment, the variants are single nucleotide variants of the selected sequence.

The probe may include a sequence complementary to the selected sequence. In one embodiment, the probe has a length equal to, or no more than 25% greater than, the selected sequence. The probe may also be shorter than the longest analyte molecule, but it is of a length effective to form a stable duplex with at least one analyte molecule under the conditions of the separation. An example is a separation wherein variations in length and/or sequence among the analyte molecules occur within a given subregion, e.g. at or near a terminus of the analyte molecule, and the probe is effective to stably hybridize to this subregion under the conditions of the analysis. Preferably, the probe is effective to form a stable duplex with a plurality of or all of the analyte molecules, and such duplexes are separated from each other and from single stranded species within the charge bearing medium.

For example, the population may contain analyte molecules which are N−1 deletion variants of the selected sequence, and the probe is effective to stably hybridize to at least a plurality of such analyte molecules, under the conditions of the separation, at a region of the analyte molecule containing a deletion site.

In another embodiment, the probe has a sequence and length identical to that of an N−1 deletion variant of the selected sequence, and the analysis conditions are such that the probe hybridizes to only that N−1 deletion variant.

In a further embodiment, the subregion in which length and/or sequence variation occurs is at or near a terminus of the analyte molecules, and the probe comprises a labeling moiety at the terminus which hybridizes to said analyte terminus. The labeling moiety is preferably a fluorescent moiety, such as fluorescein.

The charge bearing support can be an ion exchange medium, wherein the separating of step (b) comprises passing an eluant through the medium, or an electrophoresis medium, wherein the separating of step (b) comprises applying an electric field between opposing boundaries of the medium. The electrophoresis medium may be a non-sieving medium. The medium may also be one which includes a superimposed pH gradient, i.e. for use in isoelectric focusing.

Preferably, the analyte molecules are composed of linked subunits of which at least 75% are uncharged; in one embodiment, all of the subunits are uncharged. Examples of analyte molecules include peptide nucleic acids, phosphotriester oligonucleotides, methylphosphonate oligonucleotides, morpholino oligomers, and chimeras of any member of this group with another member or with DNA, 2'-O-alkyl RNA, or 2'-O-allyl RNA. In a preferred embodiment, the analyte molecules are morpholino oligomers, preferably having phosphoramidate and/or phosphorodiamidate intersubunit linkages. The probe is preferably DNA, RNA, 2'-O-alkyl RNA, 2'-O-allyl RNA, phosphorothioate DNA, or a chimera of any of these, and is most preferably DNA. In carrying out the separation, the probe is preferably present in the mixture at a concentration greater than necessary to hybridize with every analyte molecule in the population.

In one embodiment, the method further comprises the step of detecting and quantitating a duplex of a labeled probe with at least one target analyte molecule in the population. In another embodiment, the method further comprises the step of isolating at least one probe/analyte duplex.

These and other objects and features of the invention will become more fully apparent when the following detailed description of the invention is read in conjunction with the accompanying drawings.

BRIEF DESCRIPTION OF THE DRAWINGS

FIGS. 2A-A to 2E-E show the repeating subunit segment of exemplary morpholino oligomers, designated A-A through E-E, constructed using subunits A-E, respectively, of FIG. 1;

FIG. 3 illustrates hybridization of different-length uncharged analyte oligomers with a complementary charged nucleic acid, e.g. DNA, having a length equal to that of the full length analyte oligomer;

FIG. 4A illustrates hybridization of different-length uncharged analyte oligomers with a complementary charged nucleic acid, e.g. DNA, having a length sufficient to stably hybridize to a truncated terminus of the analyte molecules, and containing an optional non-hybridizing segment (represented by NNNN);

FIG. 4B illustrates hybridization of a deletion variant uncharged analyte oligomer with a complementary charged nucleic acid, e.g. DNA, having a length sufficient to stably hybridize to a region of the analyte molecule in which the deletion occurs;

FIG. 7, N-C; FIG. 8, N-G; and FIG. 9, N-T);

In FIG. 3, the following sequences are employed: The first "uncharged" sequence is ACG TTG AGG GGC ATC GTC GC, represented herein as SEQ ID NO: 1. (This sequence is antisense to a human c-myc gene sequence, corresponding to nucleotides 2551-2570 of Genbank Acc. No. X00196.) All of the "charged" sequences in this Figure are the complement of SEQ ID NO: 1. The subsequent "uncharged" sequences in FIG. 3 are fragments of SEQ ID NO: 1, represented herein as SEQ ID NO: 3 (ACG TTG AGG GGC ATC GTC), SEQ ID NO: 4 (ACG TTG AGG GGC ATC G), SEQ ID NO: 5 (ACG TTG AGG GGC AT), SEQ ID NO: 6 (GTT GAG GGG CAT), and SEQ ID NO: 7 (TGA GGG GCA TCG TCG C).

In FIG. 4A, the following sequences are employed: The first "uncharged" sequence is ACG TTG AGG GGC ATC GTC GC, represented herein as SEQ ID NO: 1. The subsequent "uncharged" sequences in FIG. 4A are fragments of SEQ ID NO: 1, represented herein as SEQ ID NO: 3 (ACG TTG AGG GGC ATC GTC) and SEQ ID NO: 4 (ACG TTG AGG GGC ATC G). All of the "charged" sequences in this Figure are fragments of the complement of SEQ ID NO: 1 plus an additional sequence NNNN, where N is any nucleotide, represented herein as SEQ ID NO: 8 (NNNN GCG ACG ATG CCC, written 5' to 3').

In FIG. 4B, the following sequences are employed: The first "uncharged" sequence is ACG TTG AGG GGC ATC GTC GC, represented herein as SEQ ID NO: 1. The subsequent "uncharged" sequence in FIG. 4B is a deletion variant of SEQ ID NO: 1, represented herein as SEQ ID NO: 10 (ACG TTG AGG GGC ATC TCG C). Both of the "charged" sequences in this Figure are a fragment of the complement of SEQ ID NO: 1, represented herein as SEQ ID NO: 9 (CGA CGA TGC C, written 5' to 3').

DETAILED DESCRIPTION OF THE INVENTION

I. Definitions

Figure 1A:
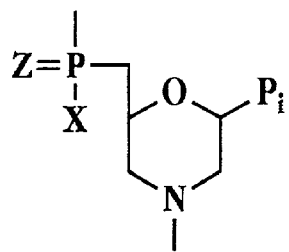
FIG. 1 shows several preferred subunits having 5-atom (A), six-atom (B) and seven-atom (C-E) linking groups suitable for forming morpholino oligomers.

The terms below have the following meanings unless indicated otherwise.

An "oligomeric" molecule, as used herein, is an oligonucleotide analog having about 8 to 100, preferably about 10 to 50, and more preferably about 10 to 30, nucleotide subunits.

Oligonucleotides or their analogs are described as "complementary" to one another when hybridization, or duplex formation, occurs between two single-stranded oligonucleotides or analogs. Complementarity (the degree to which one oligonucleotide or analog is complementary with another) is quantifiable in terms of the proportion of bases in opposing strands that are expected to form hydrogen bonds with each other, according to generally accepted base-pairing rules. In the context of the present invention, the charged nucleic acid or analog may be 100% complementary to the analyte sequence, or it may be near-complementary, e.g. including one or more mismatches or deletions, as long as the duplex formed between the charged oligomeric probe and uncharged analyte is sufficiently stable to be eluted from the separation medium in duplex form. In such cases, the probe and analyte are "stably hybridized" or form a "stable duplex" under the condition of the analysis. In particular, N−1 deletion sequences of PMO's were found to be separable by hybridization with the N-mer charged nucleic acid, as demonstrated below.

An "unhybridized" segment of DNA, or another charged oligomer, in a duplex can refer to a terminal single stranded portion as well as an internal "loop" at a deletion or mismatch site (e.g. as in FIG. 4B).

A "subunit" of an oligonucleotide or oligonucleotide analog refers to one nucleotide (or nucleotide analog) unit of the oligomer. The term may refer to the nucleotide unit with or without the attached intersubunit linkage, although, when referring to a "charged subunit", the charge typically resides within the intersubunit linkage (e.g. a phosphodiester or phosphorothioate linkage).

An "uncharged" subunit, as used herein, is one that is uncharged at near or near-neutral pH, corresponding to a pH range of about 5 to about 9. The subunit linkages may also remain uncharged at pH's outside this range. However, the pH must be above that at which C and A bases ionize (about 3) and below that at which G and T bases ionize (about 11). The analyses disclosed herein are preferably run at near or near-neutral pH, as defined above. When a fluorescein label is used, mildly basic pH (i.e. from 7 to 9) is preferred.

A "charged" subunit is one which is charged at neutral or near-neutral pH, as defined above. An example is a phosphodiester (native DNA) or phosphorothioate-linked subunit.

A "morpholino oligomer" is an oligonucleotide analog composed of morpholino subunit structures of the form shown in FIG. 1, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 1B:
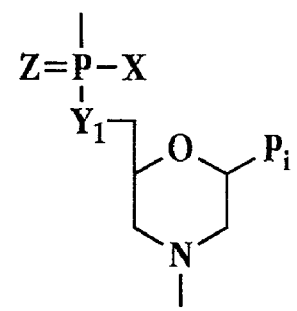
Figure 1C:
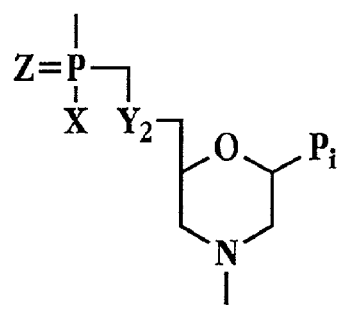
Figure 1D:
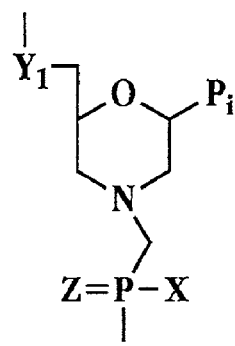
Figure 1E:
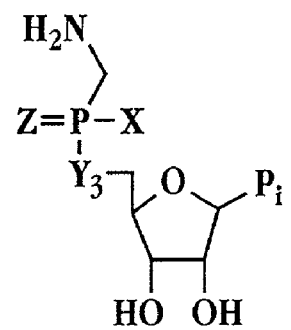

The subunit shown FIG. 1B is used for 6-atom repeating-unit backbones, as shown at B-B in FIG. 2. In these structures, the atom $Y_1$ linking the 5' morpholino carbon to the phosphorus group may be sulfur, nitrogen, carbon or, preferably, oxygen. The X moiety pendant from the phosphorus is any stable group which does not interfere with base-specific hydrogen bonding. Preferred groups include alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl (C1 to C6) substitution, and the cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is composed of morpholino subunit structures of the form shown in FIG. 2B-B, where the structures are linked together by phosphorodiamidate linkages, where X=NH$_2$, NHR, or NR$_2$ (where R is lower alkyl, preferably methyl), Y=O, and Z=O, joining the morpholino nitrogen of one subunit to the 5' exocyclic carbon of an adjacent subunit, $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 2B-B, X=lower alkoxy, such as methoxy or ethoxy, Y=NH or NR, where R is lower alkyl, and Z=O.

In a "peptide nucleic acid", the deoxyribose phosphodiester units of an oligonucleotide backbone are replaced with polyamide linkages. Proper backbone spacing is attained by the use of 2-aminoethyl glycine units, with a nucleotide base attached to each 2-amino group via a methylenecarbonyl group.

A "2'-O-allyl (or alkyl) modified oligonucleotide" is an oligoribonucleotide in which the 2' hydroxyl is converted to an allyl or alkyl ether, respectively. The alkyl ether is typically a methyl or methoxyethyl ether.

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Lower alkyl" refers to an alkyl radical of one to six carbon atoms, and preferably one to four carbon atoms, as exemplified by methyl, ethyl, isopropyl, n-butyl, isobutyl, and t-butyl.

II. Separation Method

The invention provides a method of separating and/or analyzing a population of substantially uncharged oligomeric molecules, referred to herein as analyte molecules. A "substantially uncharged" oligomeric molecule, in the context of the invention, is one in which either all of the subunits are uncharged (at neutral or near-neutral pH, i.e. about 5 to about 9), or a sufficient number are uncharged, such that duplexes of different-length analyte molecules with a charged oligomer (e.g. DNA) are separable by the separation methods described herein. Preferably, greater than 50% of the subunits, more preferably greater than 75%, and most preferably greater than 90%, are uncharged. In one embodiment, all of the subunits of the polymer are uncharged. The analyte molecules are oligonucleotide analogs, in the sense that they include a backbone which supports a sequence of base-pairing moieties which are effective to hybridize, via Watson-Crick base pairing, with bases in a complementary probe.

The analyte molecules may be of different lengths, such as in a mixture of different-length fragments of the same "parent" sequence (N-mer), as may be produced from a synthetic preparation or a degradation of a full-length polymer. Internal deletion variants or mutation variants, i.e. variants in which a given nucleotide is absent or is substituted with a different nucleotide, respectively, may also be present, as well as internal insertion variants. (Note that an N–1 or N+1 fragment may also be considered a terminal deletion or terminal insertion, respectively.) Such variants typically vary from the "parent" sequence by at most one variation per about 8 nucleotides. In one embodiment, the variants are single nucleotide variants of the selected sequence. Resolution of same-length oligomers differing in sequence only by deletion of one nucleotide at various positions, that is, different N–1 species of a selected sequence, is illustrated in the Examples below. Separation of single position variant sequences is also contemplated.

Separation is based on formation of duplexes between the various uncharged, or substantially uncharged, oligomeric molecules and a complementary charged oligonucleotide probe, which is preferably a DNA molecule. In the following discussion, the charged oligonucleotide probe is referred to as DNA; however, it is understood that RNA or charged oligonucleotide analogs may also be used as probes.

In one embodiment of the method, the analyte mixture contains a mixture of different-length fragments of the same sequence (which can include the full length sequence), and the DNA molecule is of a length equal to, or somewhat greater than, the expected length of the longest analyte molecule in the population, and has a sequence complementary (or near complementary) to the full length of the longest analyte molecule. (Longer probes, e.g. up to about 25% longer than the longest analyte molecule, can also be used.) Depending on the length of the analyte molecule, the molecule:DNA duplex will thus either be fully double stranded or will include some length of single stranded, unhybridized DNA, as shown, for example, in FIG. 3.

As an example, in an anion exchange HPLC separation of different length fragments of a morpholino oligomer having a given sequence, the single stranded oligomer, which is uncharged, would be retained least on the anion exchange column. The complementary DNA possesses a charged phosphodiester backbone and is conformationally unrestricted in single stranded form. It is therefore retained longest on the column, as it is able to maximize the interaction with the positively charged stationary phase. (Such unrestricted charges are illustrated by boldfaced negative charges in FIG. 3). An oligomer:DNA duplex has the same charge as the unhybridized DNA, but some or all of the DNA backbone is conformationally constrained by the duplex structure, which prevents optimal interaction of the backbone charges with the stationary phase (as illustrated by non-boldfaced negative charges in FIG. 3). The duplexes therefore elute between unbound PMO and DNA, at a rate depending on the amount of unconstrained single stranded DNA. Such separation is demonstrated in the Examples below.

In the case of internal deletion sequences, an unhybridized loop of DNA will occur at different locations in the duplexes, at the position of the deletion, as illustrated in FIG. 4B. While resolution is generally not as great as for different length sequences, where duplexes include some length of single stranded DNA, such deletion sequences can also be resolved, as shown in Example 2.

The separation processes can also be carried out using DNA molecules which are shorter than the longest expected analyte molecule. In this case, the DNA molecule has a sequence which hybridizes to a portion of the analyte molecules, where the portion includes the region of each analyte molecule in which variation among analyte molecules is expected, and is of a length effective to form a stable duplex. For example, when the analyte molecules differ from one another by truncation at a given terminus, the resulting duplexes will differ in terms of the unhybridized portion of charged DNA, as illustrated in FIG. 4A. As shown in FIG. 4A, the DNA may also include a short non-hybridizing terminal sequence (represented in the Figure by NNNN).

An advantage of this variation is an expected increase in resolution, particularly of N-1 mer deletion sequences. A DNA which hybridizes only to the portion of the analyte molecule containing a truncation or deletion, as shown in FIGS. 4A-B, is expected to provide greater resolution than a DNA which hybridizes to the entire molecule, since the proportion of "non-specific" interactions relative to discriminating interactions is reduced. Accordingly, this variation is most suitable for resolution of mixtures in which variation in length and/or sequence is expected to occur largely at a single terminus or within a specific region of the oligomer.

It has also been found that the separation of the duplex of an N-1 deletion variant species from that of the full length "parent" oligomer is enhanced when (1) the deletion occurs at or near a terminus of the oligomer (e.g. the 5' end) and (2) the probe used to form the duplex contains a labeling moiety, e.g. a fluorescent moiety such as fluorescein, at the hybridizing terminus (in this case, the 3' end). Similar enhanced separation is observed when the N-1 deletion occurs at or near the 3' end of the analyte oligomer, and the probe is so labeled at the 5' end.

The probe may also be specifically targeted to a particular N-1 species, being of the same length and sequence of that species, and the analysis carried out under sufficiently stringent hybridization conditions (typically with respect to temperature) such that the probe stably hybridizes to only that N-1 species. Alternatively, the analysis may be carried out under somewhat less stringent conditions, such that the probe may stably hybridize to the N-mer and some other N-1 species, and the duplexes separated on the basis of their different interactions with the charge bearing separation medium.

In performing the separation or analysis, a mixture of the population of molecules to be separated and the charged probe molecule, preferably a labeled DNA, is formed under appropriate hybridizing conditions, and the mixture is applied to a charge bearing separation medium, preferably an anion exchange column. When it is desired that the DNA probe stably hybridizes with every analyte molecule having a complementary or near-complementary region, the probe is preferably added in excess. The duplexes are then separated within the medium, typically by elution, at near or near neutral pH (between about 5 and about 9).

The analysis is generally carried out at a temperature sufficiently below the $T_m$ of the duplexes of the desired analytes to ensure that they remain in duplex form during separation. Preferably, this temperature is about 20° below the lowest expected $T_m$. However, higher temperatures can be used to increase stringency, e.g. when it is desired that the probe stably hybridizes to only selected species, as described above.

The method allows detection of low levels of an analyte by hybridization with labeled DNA. The label is preferably a fluorescent label, such as fluorescein, and is typically attached at a terminus of the DNA probe. An internal standard having a sequence which includes or is a fragment of that of the analyte, but is of a different length, can be used for quantitation of the analyte. Example 3 demonstrates the use of this method in detecting very low levels (approx. 10 ng) of a particular PMO in a plasma sample.

III. Analyte Molecules

As stated above, a "substantially uncharged" oligomeric molecule, in the context of the invention, is an oligonucleotide analog in which all of the nucleotide subunits are uncharged at near or near-neutral pH (about pH 5 to about pH 9), or a sufficient number are uncharged at said pH such that duplexes of different-length molecules with a charged oligomer, such as DNA, are separable by the separation methods described herein.

Examples of well known uncharged oligonucleotide analogs include peptide nucleic acids, phosphotriester oligonucleotides, methyl phosphonate oligonucleotides, and morpholino oligomers having uncharged intersubunit linkages. In a preferred embodiment, the analyte oligomers are morpholino oligomers, having uncharged intersubunit linkages. Such linkages are illustrated in FIGS. 2AA-2EE. In preferred embodiments, the linkages are selected from a phosphorodiamidate linkage as represented by FIG. 2B-B, where $X=NH_2$, NHR, or $NR_2$ (where R is lower alkyl, preferably methyl), Y=O, and Z=O, and an alternate phosphorodiamidate linkage as also represented by FIG. 2B-B, where X=OR, Y=NH or NR, and Z=O, where R is lower alkyl. Morpholino oligomers having either of these linkages are referred to herein as PMO's.

Analyte molecules may also include chimeras of the above named oligonucleotide analogs. Also included are chimeras, e.g. alternating copolymers, with charged oligomers such as DNA, 2-O-alkyl RNA, or 2-O-allyl RNA. As noted above, it is preferred that at least 50% of the subunits of such copolymers be uncharged.

Analyte molecules not having a region complementary to the charged nucleic acid are expected to remain unhybridized and to pass through the charged medium quickly, with no charge-based separation. The present methods are most suitable, therefore, for mixtures of analyte molecules representing different fragments of the same sequence. An example is a synthetic reaction mixture, as illustrated in Example 1. This Example illustrates the use of the method in separating mixtures of several PMOs differing in length by only one subunit. Example 2 illustrates resolution of N-1 deletion sequences. Backbone cleavage of an oligomer, by biological or other routes, can also be determined by analysis of the degradation products.

IV. Charged Nucleic Acid Oligomers

The charged nucleic acid used for duplex formation is most typically DNA. However, any charged, stably hybridizing RNA or DNA analog could also be used. While the oligomer is preferably, and most conveniently, fully charged, it need only include a sufficient number of charged subunits such that its duplexes with different-length analyte molecules are separable by the separation methods described herein. For convenience and simplicity of analysis, a single species (i.e. a single length and sequence) of charged nucleic acid or analog is preferably used.

Charged nucleic acid analogs which could be used include modified DNA, RNA, modified RNA such as 2'-O-alkyl RNA or 2'-O-allyl RNA, and phosphorothioate DNA. "Modified" in this sense includes modifications to the ribose sugar group or base pairing moieties, e.g. C-2-methyl or -propynyl substituted bases, as long as such modifications do not interfere with hybridization or with resolution of the charged:uncharged duplexes.

In accordance with the separation strategy, the DNA or charged analog has a length and sequence such that its duplexes with different analyte molecules differ with respect to the presence, length and/or position of the unhybridized portion (i.e. single stranded or internal loop) that results upon duplex formation. It is complementary or near complementary to at least a portion of the sequence of the longest analyte molecule intended to be separated. It may also include a terminal nonhybridizing sequence (see e.g. FIGS. 4A-B).

In one embodiment of the method, the DNA has a length equal to or greater than the expected length of the longest analyte molecule intended to be separated. However, as described above, shorter DNA may be used, particular when the expected difference(s) among analyte molecules are predominantly within a predicted subregion of the analyte molecules.

While the DNA may be longer than the longest analyte molecule, and/or may include a nonhybridizing sequence, increasing the length of unhybridized DNA in the duplexes results in longer retention times and increased non-specific interactions with the charge bearing medium. For most applications, therefore, the DNA is no more than about 25% longer than the expected length of the longest analyte molecule.

For detection purposes, the probe is labeled, preferably with a fluorescent label such as fluorescein, and preferably at the 5' or 3' terminus of the probe.

V. Separation Techniques

Any charge-based separation technique useful for separating charged biopolymers may be used to separate the charged:uncharged duplexes formed by mixing the substantially uncharged analyte molecules with the charged nucleic acid or analog, in accordance with the invention. Such techniques are well known in the art. In general, the mixture is applied to a charge-bearing separation medium for separation, in accordance with procedures known in the art. Separation is carried out at near or near-neutral pH, under conditions such that duplexes between the DNA and analyte molecules are sufficiently maintained for separation purposes. In a preferred method, the charge-bearing medium is an ion exchange resin, specifically an anion exchange column, and elution is carried out at neutral or near neutral pH, as in the Examples below.

In other embodiments, the charge bearing separation medium is an electrophoresis medium. Such media are charged by applying an electric field between opposing boundaries, according to procedures well known in the art. Established methods of separating charged molecules in such media include capillary electrophoresis, gel electrophoresis, such as PAGE (polyacrylamide gel electrophoresis), and isoelectric focusing, which employs a superimposed pH gradient. The present method may employ a non-sieving medium, that is, one that does not differentiate molecules by size. Examples are non-gel capillary electrophoresis and isoelectric focusing.

VI. Applications

In a representative analysis, a DNA molecule, typically fluorescently labeled, which is complementary or near complementary to at least some region of the longest expected analyte molecule, as described above, is mixed with a sample containing the analyte molecules. The sample may be a biological sample, e.g. a plasma, urine or tissue lysate sample, prepared for analysis in accordance with known isolation protocols, e.g. as described below for plasma in Example 3. Alternatively, it may be a product mixture from an oligonucleotide synthesis. A large excess of DNA can be used, to ensure complete formation of duplexes, since the free DNA migrates sufficiently distant from the duplexes that it does not interfere. Preferably, the DNA is recovered for further use, particularly in the case of preparative separations of reaction mixtures.

Figure 5A:
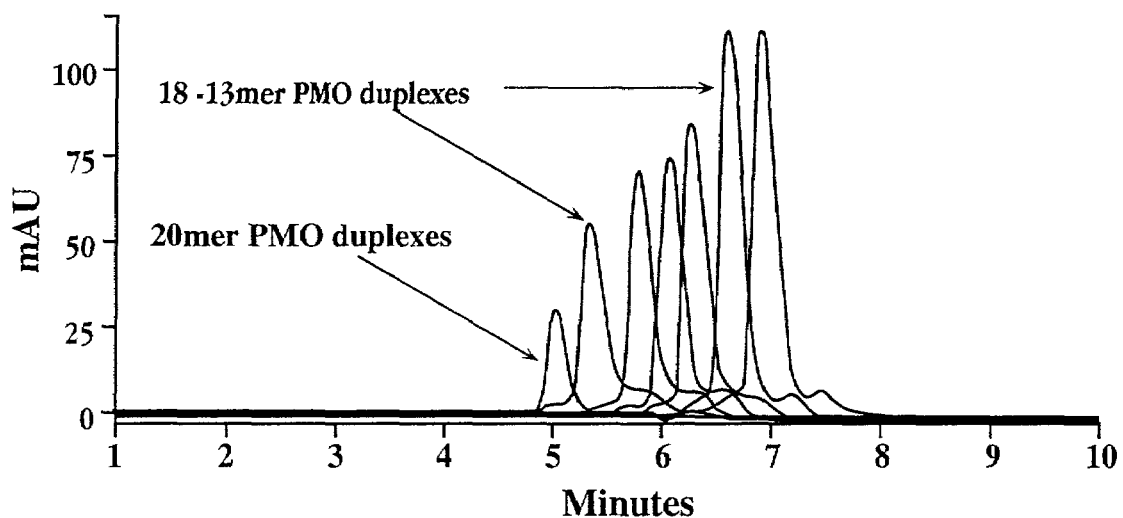
FIGS. 5A-5B are HPLC chromatograms showing resolution by anion exchange of duplexes of DNA with 13- to 20-mer morpholino oligomers.
Figure 5B:
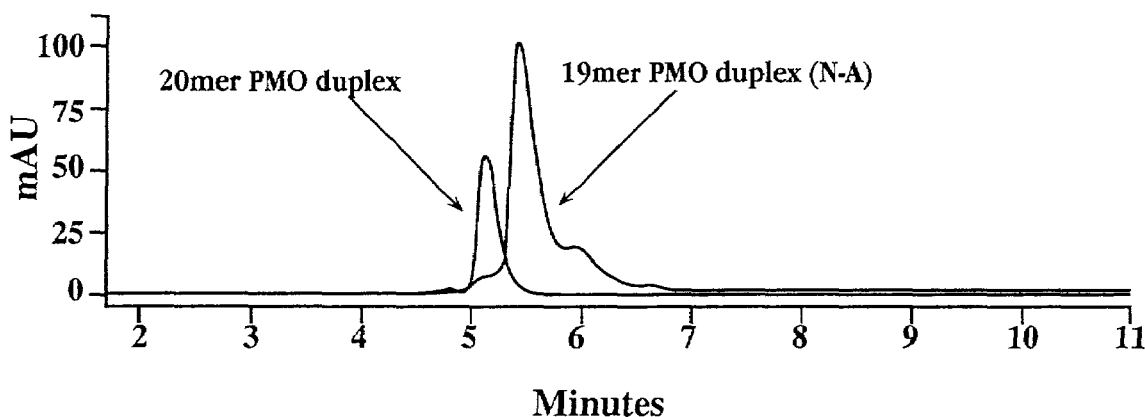
Figure 6:
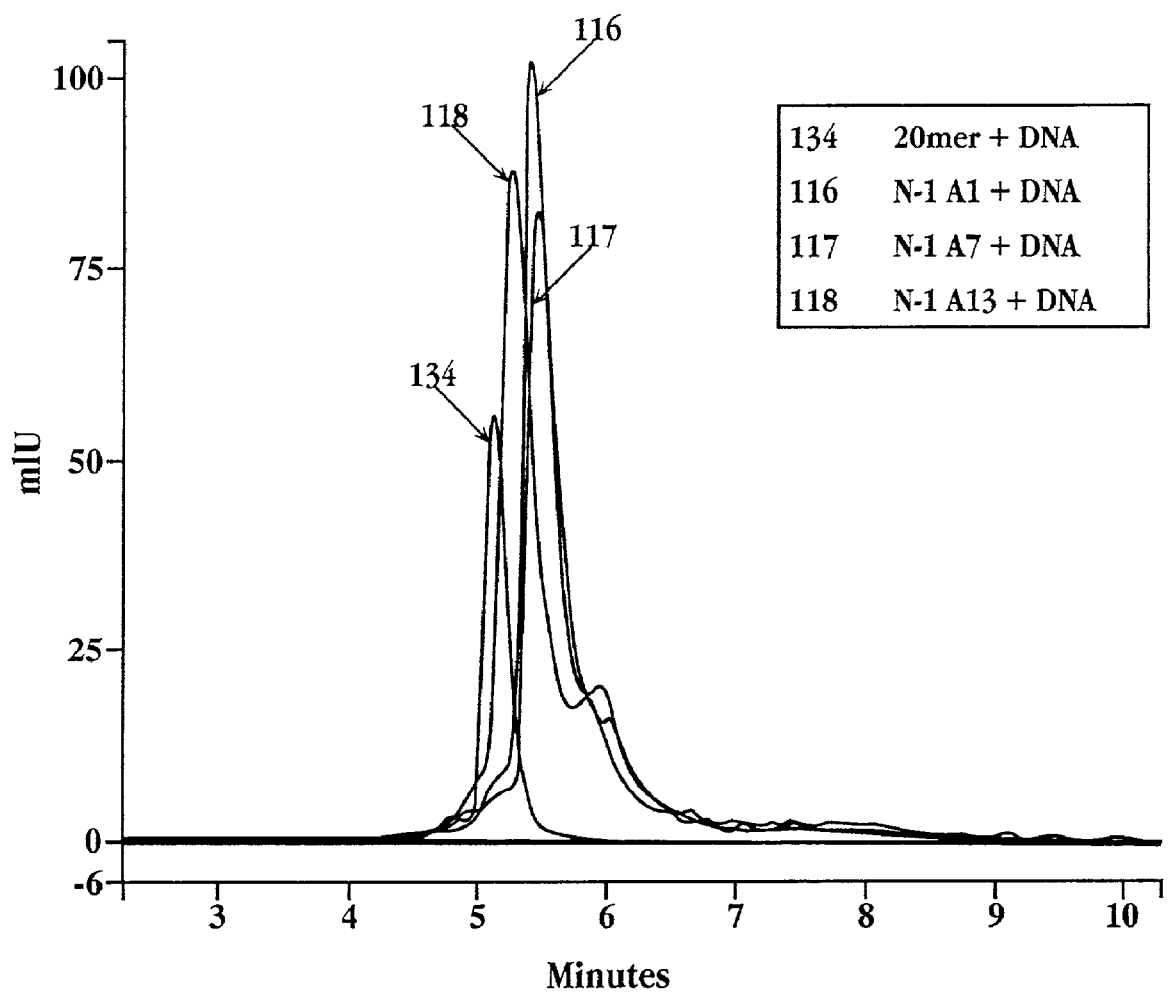
FIGS. 6-9 are overlays of HPLC chromatograms showing anion exchange retention times of duplexes of DNA with various N−1 deletion sequences of a 20-mer morpholino oligomer (FIG. 6, N-A.
Figure 7:
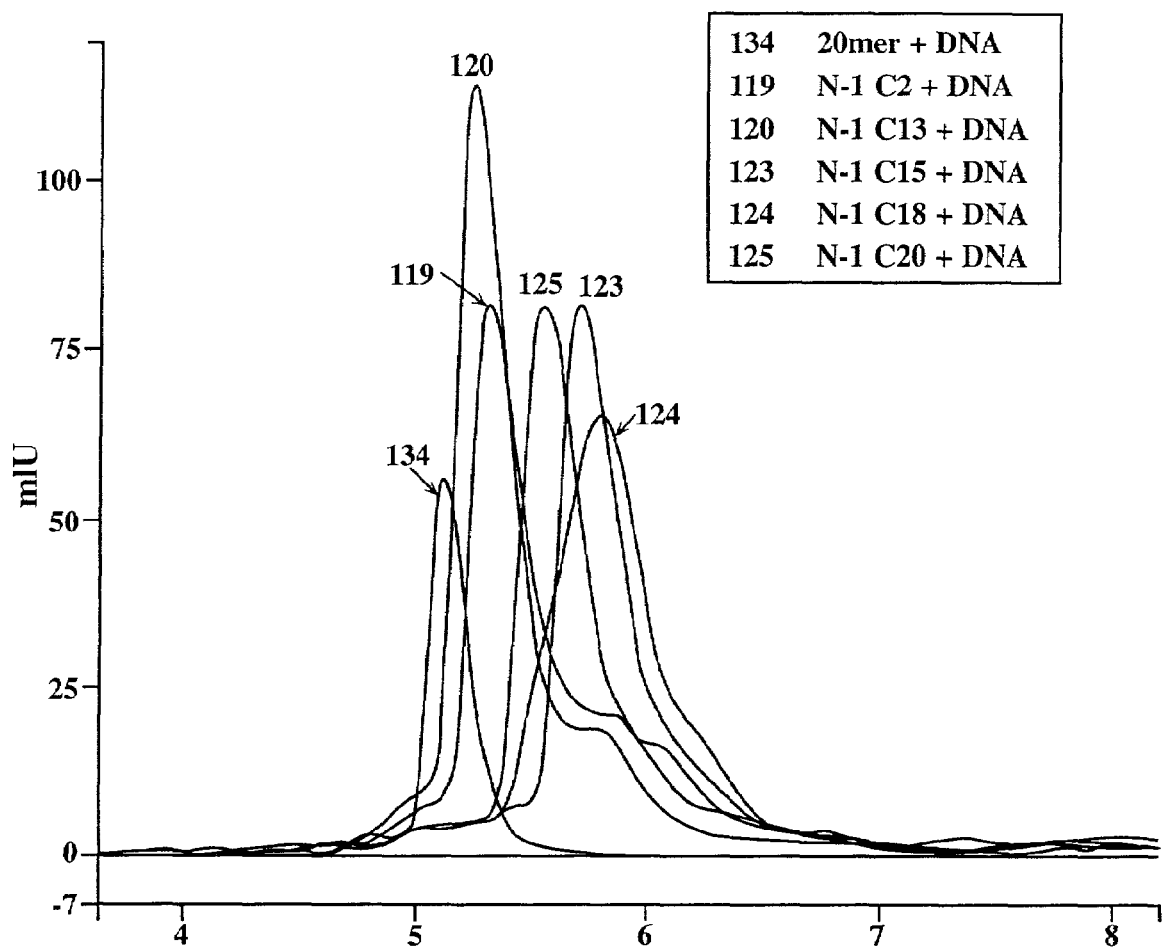
Figure 8:
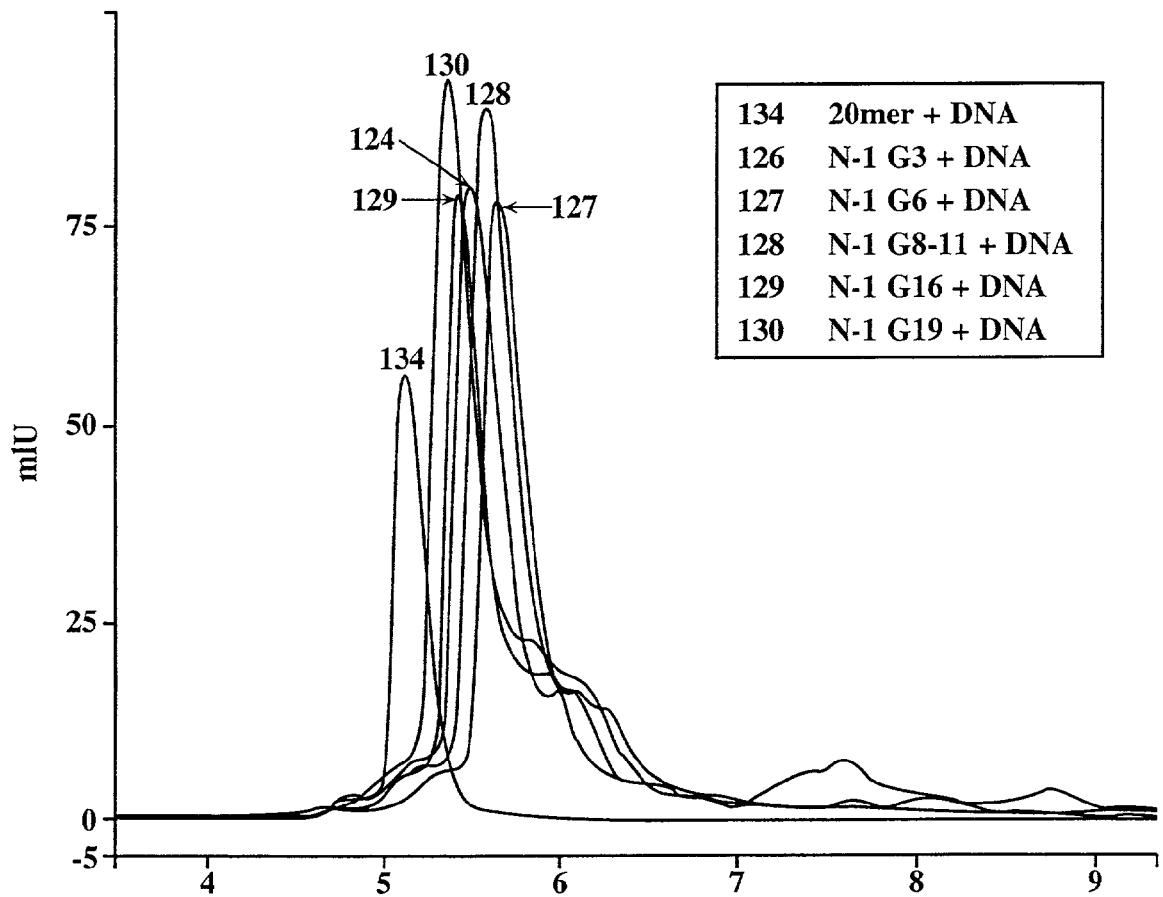
Figure 9:
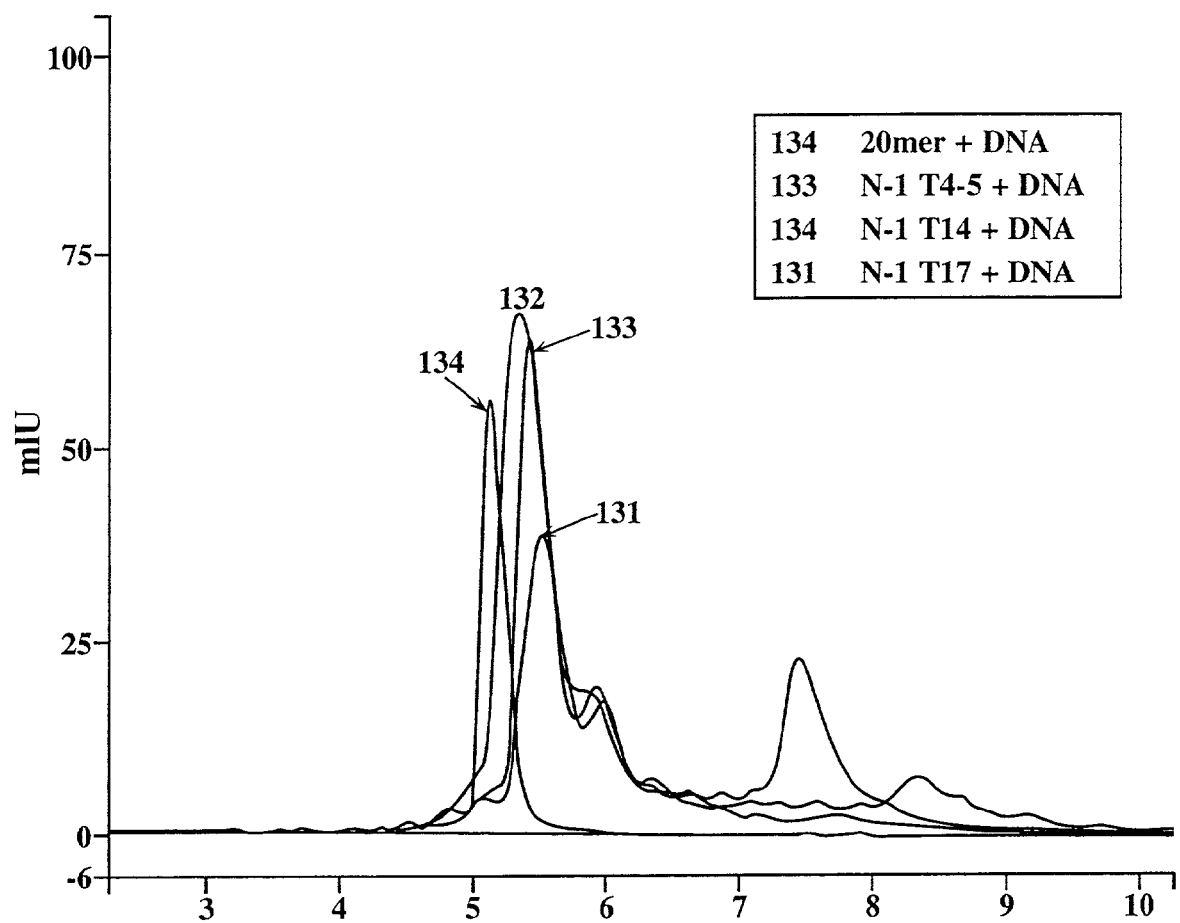

Example 1 below illustrates the separation, by ion exchange, of 13-mer to 19-mer truncated species from a 20-mer PMO. Separation was carried out on a Dionex DNA Pac™ ion exchange column, using eluents having a pH range of 7 to 9. As shown in FIGS. 5A-B, the species, differing by one nucleotide in length, were clearly resolved.

Example 2 shows the separation of various 19-mer N–1 deletion species, in which a single nucleotide was deleted from the parent 20-mer. Differences in retention times of the different 19-mers are shown in FIGS. 6-9.

Figure 12:
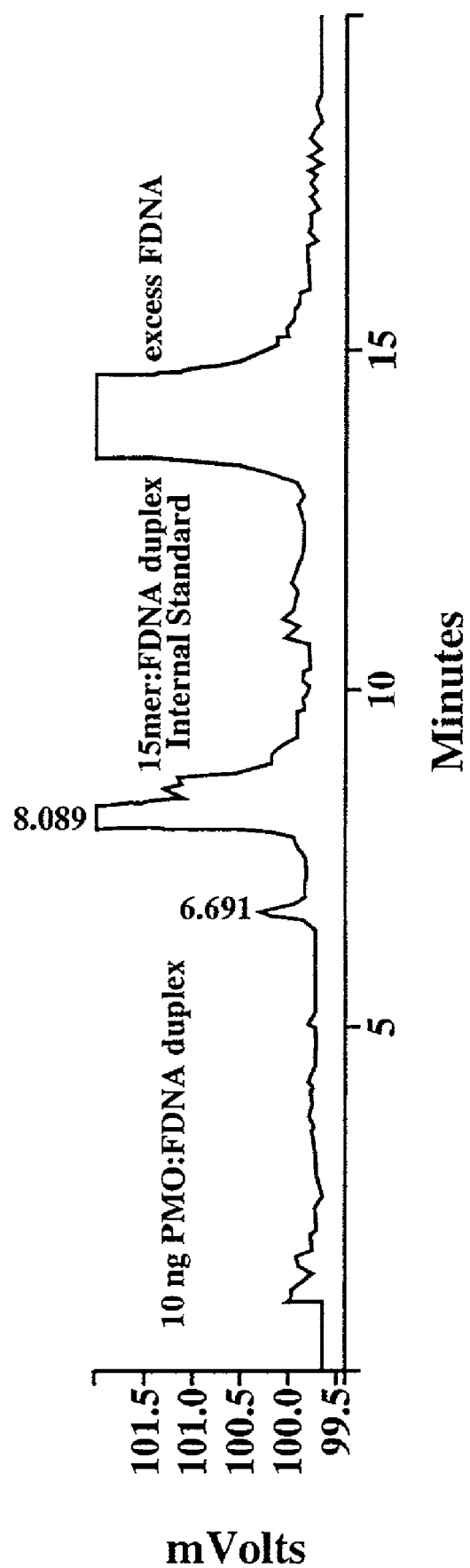
FIG. 12 is an HPLC chromatogram showing detection of approx. 10 ng of target PMO in a plasma sample, by resolution of its duplex with DNA from an internal standard: DNA duplex and excess DNA.

In all of these analyses, very little background from the sample matrix was observed, and very low levels of analyte could be detected and quantitated. The sensitivity of the method in detecting a target PMO in a plasma sample is demonstrated in Example 3. A calibration curve (FIG. 10) was prepared using 200 μL plasma samples and increasing amounts of a 15-mer standard, shown in FIG. 11. In analysis of the plasma sample, the 15-mer internal standard was cleanly separated from the 20-mer analyte, which was detected at a level of 10 ng, or 50 ng/mL (FIG. 12).

EXAMPLES

The following examples illustrate but are not intended to limit the invention.

Materials and Methods

DNA was purchased from Hybridon Specialty Products. The analyte, a PMO having the sequence ACG TTG AGG GGC ATC GTC GC (SEQ ID NO: 1), and a 15-mer fragment as internal standard (FIG. 11) having the sequence GAG GGG CAT CGT CGC (SEQ ID NO: 2), were prepared at AVI BioPharma according to standard methods. (SEQ ID NO: 1 is antisense to a human c-myc gene sequence, corresponding to nucleotides 2551-2570 of Genbank Acc. No. X00196.) The identity of the 15-mer was confirmed by MALDI-TOF mass spectrometry (calc. M+H 5350.6, found 5350.0).

HPLC was carried out using a Varian 9010 "inert" pump equipped with a Rainin A1-200 autosampler and connected to a Varian 9075 fluorescence detector. Data acquisition was performed using a Varian Star chromatography workstation, version 5.3. HPLC conditions were as described below.

Example 1

Resolution of 13-mer to 19-mer Truncated Species of a 20-mer PMO

A mixture of 13-mer to 19-mer truncated species and the parent 20-mer PMO, having the sequence ACG TTG AGG GGC ATC GTC GC (SEQ ID NO: 1), were resolved by complexation with a complementary 20-mer DNA. HPLC conditions were as follows:

Column: Dionex DNA Pac™ PA-100 (250×4 mm, 15μ particle size)
Mobile Phases: A: 0.025 M Tris (pH 9); B: 0.025 M Tris (pH 9)/1 M NaCl
Gradient: A:B:C 90/10 @ 0 min to 55/45 @ 20 min
Flow Rate: 1.5 mL/min
Wavelength: 254 nm
Temperature: 25° C.

As shown in FIGS. 5A-B, all species were resolved. As discussed above, the variation in retention times is believed to be attributable to the relative proportions of conformationally unrestricted and conformationally restrained charges of the respective PMO:DNA duplexes.

Example 2

Resolution of N−1 Deletion Species

In this study, the retention times of DNA duplexes with N−1 19-mer species from a 20-mer PMO having the sequence ACG TTG AGG GGC ATC GTC GC (SEQ ID NO: 1) were compared with the full length 20 mer:DNA duplex. A 0.1 OD/30.0 μL DNA solution was added to each 100.0 μL aliquot of aqueous sample containing 0.1 OD of the N−1 oligomer, and the solution was thoroughly mixed. A 10.0 μL aliquot of each resulting solution was removed and analyzed by HPLC (ion exchange) using an autosampler. HPLC conditions were as follows:

Column: Dionex DNA Pac™ PA-100 (250×4 mm, 15μ particle size)
Mobile Phases: A: water; B: 0.25M Tris buffer (pH 8); C: 1M NaCl
Gradient: A:B:C 80/10/10 @ 0 min to 45/10/45 @ 20 min
Flow rate: 1.5 mL/min
Temp: 25° C.
Detection: UV, 254 nm Retention times are given in Table 1 below. As shown, all the N−1 duplex samples eluted after the full length 20 mer:DNA duplex. FIGS. 6-9 present overlays of chromatograms showing retention times for various N−1 species for each nucleotide.

TABLE 1

| N-A Series | RT (min) | N-C Series | RT (min) | N-G Series | RT (min) | N-T Series | RT (min) |
|---|---|---|---|---|---|---|---|
| 20:20 duplex | 5.115 | 20:20 duplex | 5.115 | 20:20 duplex | 5.115 | 20:20 duplex | 5.115 |
| N-A1 | 5.410 | N-C2 | 5.311 | N-G3 | 5.483 | N-T4 | 5.416 |
| N-A7 | 5.477 | N-C12 | 5.711 | N-G6 | 5.643 | N-T14 | 5.336 |
| N-A13 | 5.262 | N-C15 | 5.551 | N-G8-11 | 5.576 | N-T17 | 5.514 |
|  |  | N-C18 | 5.797 | N-G16 | 5.422 |  |  |
|  |  | N-C20 | 5.244 | N-G19 | 5.354 |  |  |

Example 3

Quantitation of Target PMO Species in Plasma

HPLC conditions:
Column: Dionex DNA Pac™ PA-100 (250×4 mm, 15μ particle size)
Mobile Phases: A: 0.025 M Tris (pH 9); B: 0.025 M Tris (pH 9)/1 M NaCl
Gradient: A:B:C 90/10 @ 0 min to 55/45 @ 20 min
Flow Rate: 1.5 mL/min
Wavelength: 494 nm excitation; 518 detection
Temperature: 25° C.

Cynomolgus monkeys were injected i.v. with the analyte PMO, and blood samples were taken at various time intervals, as shown in Table 2. In a typical analysis, 200 μL of plasma was combined with a known amount (e.g. 500 ng) of internal standard (FIG. 11) in 10 μL of 0.025 M Tris buffer, pH 8-9. Methanol (200.0 μL) was added, and the sample was mixed using a vortex mixer. The precipitate was removed with the aid of high speed centrifugation. The supernatant was removed and the pellet washed with 100 μL Tris buffer; the wash was added to the supernatant. The mixture was heated at 70° C. for a period of 10 minutes, and the sample was once again subjected to high speed centrifugation. The supernatant was transferred and lyophilized to dryness. The dry material was reconstituted with a 100.0 μL aliquot of DNA (5'-fluorescein labeled) in 0.025 M Tris (pH 8-9) and transferred to an autosampler vial, and the entire sample was injected onto the HPLC column and analyzed.

Figure 10:
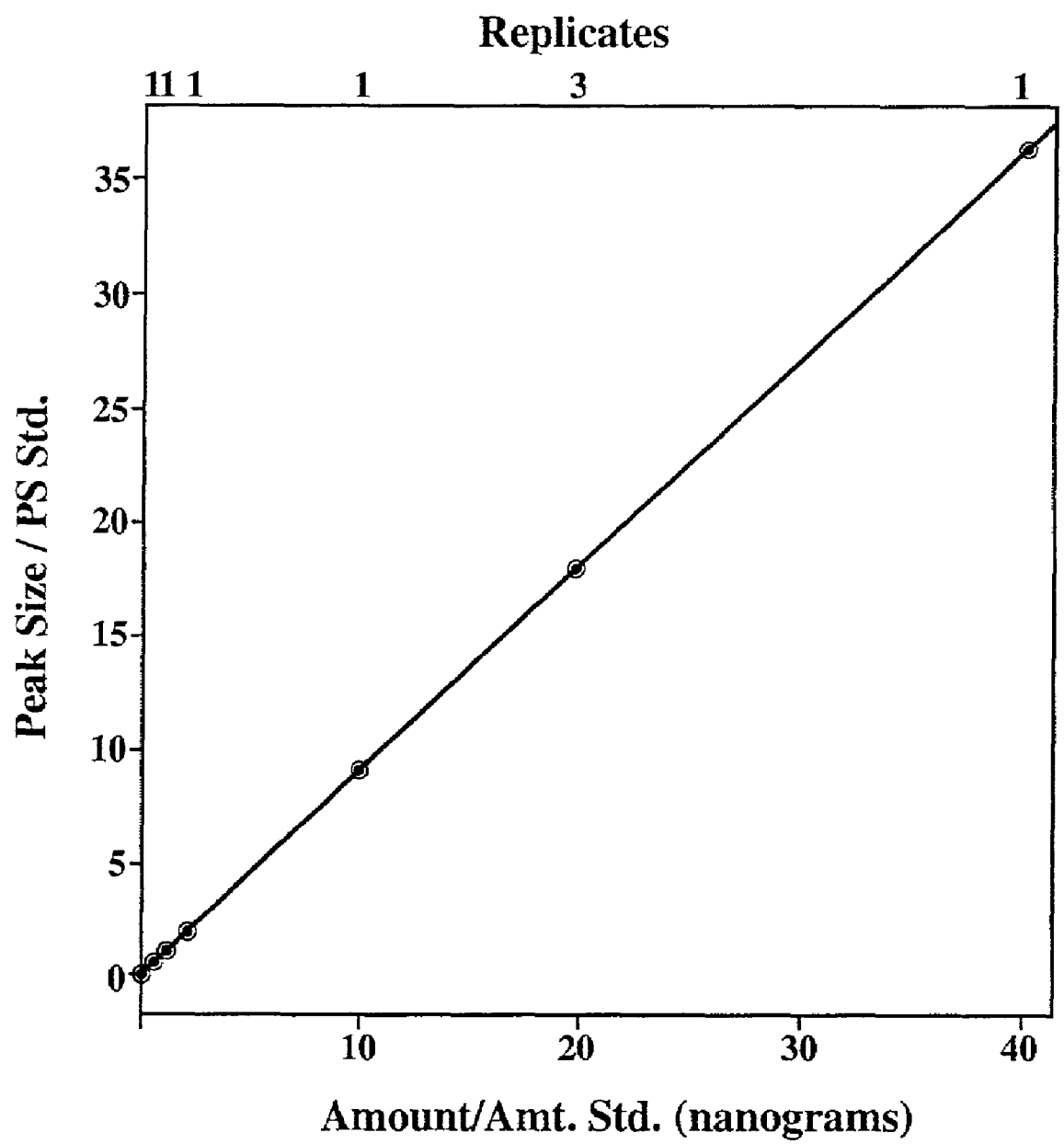
FIG. 10 is a calibration curve showing peak area vs. concentration of 20-mer PMO analytes and a 15-mer PMO internal standard, whose structure is shown in FIG. 11.

A calibration was performed by analysis of plasma standards containing from 250 to 20,000 ng of AVI-4126. The data were plotted as the ratio of analyte to internal standard signal intensities versus the ratio of analyte to internal standard concentrations. The plot is shown in FIG. 10, which shows a correlation coefficient of 0.999920.

Quantitation of the samples, based on the internal standard, is given in Table 2. A chromatogram of a representative assay is shown in FIG. 12. The level detected in this assay was 10.0 ng analyte, which corresponded to 50 ng/mL. The sensitivity of this method thus far exceeds the detection and quantitation limits of UV based methods.

TABLE 2

Quantitation of PMO in Plasma of Cynomolgus Monkeys Following i.v. Injection

| Monkey ID | 10 min (μg/mL) | 2 h (μg/mL) | 6 hr (μg/mL) | 24 hr (μg/ml) |
|---|---|---|---|---|
| 29M | — | — | — | — |
| 38M | 105.37 | 68.025 | 45.33 | 14.895 |
| 39F | 105.685 | 49.755 | 32.015 | 12.645 |
| 40M | 92.505 | 49.895 | 29.81 | 17.575 |

While the invention has been described with reference to specific methods and embodiments, it will be appreciated that various modifications may be made without departing from the invention.

It is claimed:

1. A method of separating a population of duplexes, each comprising one of a population of different, substantially uncharged oligomeric analyte molecules and a specific probe molecule, wherein said substantially uncharged analyte molecules are oligonucleotide analogs composed of linked subunits of which at least 90% are uncharged, and said specific probe molecule is a fully charged nucleic acid or fully charged nucleic acid analog, the method comprising:

(a) applying to an ion exchange medium a mixture of (i) the different substantially uncharged analyte molecules and (ii) the specific probe molecule, under conditions such that the probe forms stable duplexes with a plurality of or all of the different substantially uncharged analyte molecules, thereby forming a plurality of different probe-analyte duplexes, which differ from each other with respect to the presence, length or position of an unhybridized portion of the probe molecule, and (b) separating said different probe-analyte duplexes from each other and from single stranded analyte or probe molecules within the medium.

2. The method of claim 1, wherein each analyte molecule has a nucleotide sequence selected from the group consisting of a selected sequence, different length fragments of the selected sequence, internal deletion or insertion variants of the selected sequence, mutation variants of the selected sequence, and combinations thereof.

3. The method of claim 2, wherein said deletion, insertion or mutation variants contain at most one such deletion, insertion or mutation per 8 nucleotides of the selected sequence.

4. The method of claim 2, wherein the probe includes a sequence complementary to the selected sequence.

5. The method of claim 4, wherein the probe has a length which is equal to, or up to 25% greater than, the length of the selected sequence.

6. The method of claim 2, wherein the probe includes a sequence complementary to an N−1 internal deletion variant of the selected sequence, N being the length in nucleotides of the selected sequence.

7. The method of claim 6, wherein the probe has a length equal to said N−1 deletion variant of the selected sequence.

8. The method of claim 7, wherein said conditions are such that said probe hybridizes to only said N−1 deletion variant.

9. The method of claim 2, wherein variations in sequence or length among said analyte molecules occur within a given subregion of said selected sequence, and the probe is effective to stably hybridize to said subregion under the conditions of said applying and separating.

10. The method of claim 9, wherein the population contains analyte molecules which are N−1 deletion variants of the selected sequence, and the probe has a sequence and length sufficient to stably hybridize to each analyte molecule, under the conditions of said separating, at a region of the analyte molecule containing a deletion site.

11. The method of claim 1, wherein all of said subunits are uncharged.

12. The method of claim 1, wherein the analyte molecules are selected from the group consisting of peptide nucleic acids, phosphotriester oligonucleotides, methylphosphonate oligonucleotides, morpholino oligomers, and chimeras of any member of this group with another member of this group or with DNA, 2'-O-alkyl RNA, or 2'-O-allyl RNA.

13. The method of claim 12, wherein the analyte molecules are morpholino oligomers.

14. The method of claim 13, wherein said morpholino oligomers have intersubunit linkages selected from the group consisting of phosphoramidate and phosphorodiamidate.

15. The method of claim 1, wherein the probe is selected from the group consisting of DNA, RNA, 2'-O-alkyl RNA, 2'-O-allyl RNA, phosphorothioate DNA, and chimeras thereof.

16. The method of claim 15, wherein the nucleic acid is DNA.

17. The method of claim 1, wherein the probe is labeled.

18. The method of claim 17, further comprising the step of detecting and quantitating a duplex of the labeled probe with at least one target analyte molecule in the population.

19. The method of claim 1, further comprising the step of isolating at least one said duplex.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: antisense to nucleotides 2551-2570 of human c-
      myc at Genbank X00196

<400> SEQUENCE: 1
acgttgaggg gcatcgtcgc                                                    20

<210> SEQ ID NO 2
<211> LENGTH: 15
<212> TYPE: DNA
<213> ORGANISM: Artificial Sequence
<220> FEATURE:
<223> OTHER INFORMATION: fragment of SEQ ID NO: 1

<400> SEQUENCE: 2 gagggcatc gtcgc                                                          15

<210> SEQ ID NO 3
<211> LENGTH: 18
<212> TYPE: DNA
<213> ORGANISM: Artificial Sequence
<220> FEATURE:
<223> OTHER INFORMATION: fragment of SEQ ID NO: 1

<400> SEQUENCE: 3
acgttgaggg gcatcgtc                                                      18

<210> SEQ ID NO 4
<211> LENGTH: 16
<212> TYPE: DNA
<213> ORGANISM: Artificial Sequence
<220> FEATURE:
<223> OTHER INFORMATION: fragment of SEQ ID NO: 1

<400> SEQUENCE: 4
acgttgaggg gcatcg                                                        16

<210> SEQ ID NO 5
<211> LENGTH: 14
<212> TYPE: DNA
<213> ORGANISM: Artificial Sequence
<220> FEATURE:
<223> OTHER INFORMATION: fragment of SEQ ID NO: 1

<400> SEQUENCE: 5
acgttgaggg gcat                                                          14

<210> SEQ ID NO 6
<211> LENGTH: 12
<212> TYPE: DNA
<213> ORGANISM: Artificial Sequence
<220> FEATURE:
<223> OTHER INFORMATION: fragment of SEQ ID NO: 1

<400> SEQUENCE: 6
gttgaggggc at                                                            12

<210> SEQ ID NO 7

```
-continued

<211> LENGTH: 16
<212> TYPE: DNA
<213> ORGANISM: Artificial Sequence
<220> FEATURE:
<223> OTHER INFORMATION: fragment of SEQ ID NO: 1

<400> SEQUENCE: 7
tgaggggcat cgtcgc                                               16

<210> SEQ ID NO 8
<211> LENGTH: 16
<212> TYPE: DNA
<213> ORGANISM: Artificial Sequence
<220> FEATURE:
<223> OTHER INFORMATION: fragment of complement to SEQ ID NO: 1
<221> NAME/KEY: misc_feature
<222> LOCATION: (1)...(4)
<223> OTHER INFORMATION: n = A,T,C or G

<400> SEQUENCE: 8
nnnngcgacg atgccc                                               16

<210> SEQ ID NO 9
<211> LENGTH: 10
<212> TYPE: DNA
<213> ORGANISM: Artificial Sequence
<220> FEATURE:
<223> OTHER INFORMATION: fragment of complement to SEQ ID NO: 1

<400> SEQUENCE: 9
cgacgatgcc                                                      10

<210> SEQ ID NO 10
<211> LENGTH: 19
<212> TYPE: DNA
<213> ORGANISM: Artificial Sequence
<220> FEATURE:
<223> OTHER INFORMATION: deletion variant of SEQ ID NO: 1

<400> SEQUENCE: 10
acgttgaggg gcatctcgc                                            19
```